United States Patent [19]

Brett

[11] Patent Number: 5,216,923
[45] Date of Patent: Jun. 8, 1993

[54] MOBILE LABORATORY FOR ON-SITE TESTING OF INDUSTRIAL SLING

[76] Inventor: Charles W. Brett, 640 Lakes Edge Dr., Oxford, Mich. 48051

[21] Appl. No.: 832,671

[22] Filed: Feb. 6, 1992

Related U.S. Application Data

[63] Continuation of Ser. No. 528,408, May 25, 1990, abandoned.

[51] Int. Cl.⁵ .............................................. G01N 3/08
[52] U.S. Cl. ...................................................... 73/827
[58] Field of Search .................... 73/826–835, 73/837, 104, 821, 852

[56] References Cited

U.S. PATENT DOCUMENTS

| | | | |
|---|---|---|---|
| 1,141,822 | 6/1915 | Olsen | 73/828 |
| 2,321,875 | 6/1943 | Temple | 73/837 |
| 2,645,936 | 7/1953 | Albrecht | 73/821 |
| 2,824,446 | 2/1958 | Stutzer | 73/828 |
| 3,010,311 | 11/1961 | Meldrum et al. | 73/828 |
| 3,224,258 | 12/1965 | Preston | 73/831 |
| 3,286,515 | 11/1966 | Bendl | 73/829 |
| 3,879,991 | 4/1975 | Ristow et al. | 73/837 |
| 4,475,404 | 10/1984 | Rutledge et al. | 73/828 |
| 4,735,450 | 4/1988 | Fern | 73/831 |

OTHER PUBLICATIONS

Magnaflux Corp. Brochure, Oct. 1957.

*Primary Examiner*—Robert Raevis
*Attorney, Agent, or Firm*—Jay C. Taylor

[57] ABSTRACT

The procedure heretofore of transporting industrial slings annually to and from the industrial site where the sling is used and a test facility for stress testing the sling, and the concomitant withdrawal of the sling from industrial use for a day or more, are avoided by mounting the stress testing equipment on a motorized vehicle to enable such testing at the industrial site.

5 Claims, 2 Drawing Sheets

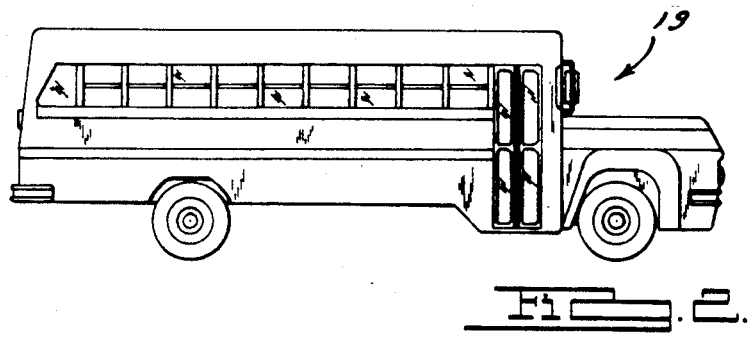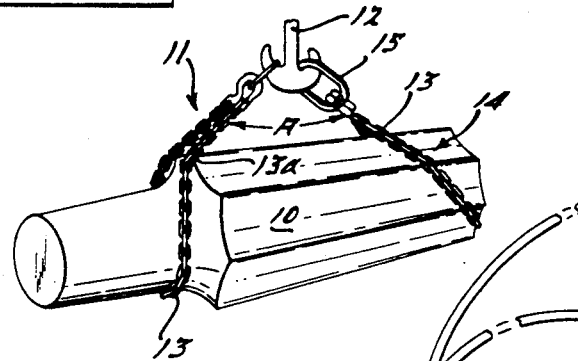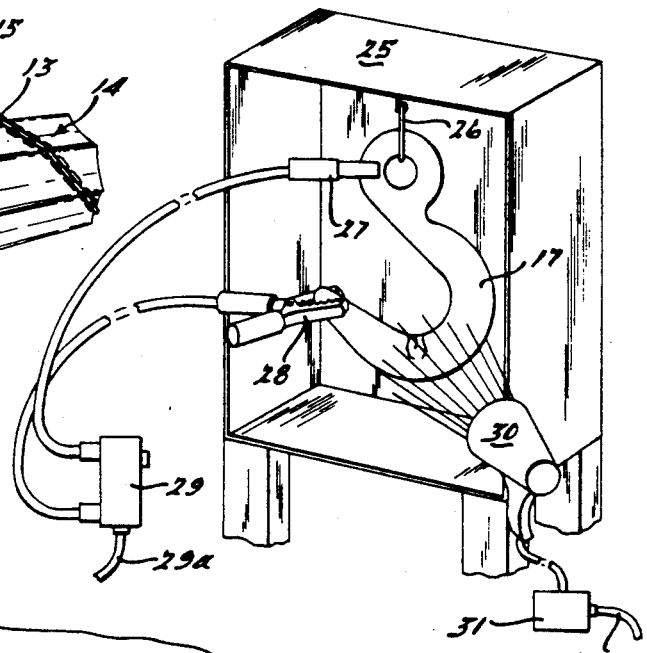

MOBILE LABORATORY FOR ON-SITE TESTING OF INDUSTRIAL SLING

This is a continuation of copending application Ser. No. 07/528,408 filed on May 25, 1990, now abandoned.

This invention relates to a method and apparatus for on-site testing of heavy duty industrial slings comprising assemblies of hooks and chains used for hoisting and conveying heavy articles, frequently weighing many tons.

BACKGROUND OF THE INVENTION

It is a commonplace in shipyards, foundries, manufacturing plants and alike, to hoist and convey heavy articles suspended from an overhead traveling crane by an assembly of hooks and chains commonly called "slings" by the art. As a consequence of misuse, overloading or improper loading, and jerky crane operation among other factors, elements of the sling become visably worn, gouged or deformed and in some situations, stressed to provide cracks not readily apparent by casual visual inspection.

Federal and State safety regulations require annual testing of the sling components by certified inspectors to insure a safety factor of at least 2:1, i.e., that a chain having a 1,000 pound rating, for example, can withstand a load of at least 2,000 pounds. Such testing requires special heavy and sophisticated equipment not available at the industrial site where the sling is used. Heretofore, private testing laboratories having such equipment have collected slings from the industrial sites for annual testing, transported the slings to a test facility, tested the sling components and if necessary and feasible, repaired the same. After being tested, the sling components are then certified as having the required 2:1 safety factor and returned to the industrial site where the sling is to be used. The annual certification usually entails a day or more downtime for the sling before it is returned to the user, who is thus loath to dispense with the sling more frequently than absolutely necessary to abide by the law, regardless that more frequent thorough testing is often advisable for slings in constant demanding use.

Cleaning and visual inspection at frequent intervals, depending upon the extent and severity of use, is recommended by the sling manufacturer, and in fact, where slings are in constant severe use, daily cleaning and inspection is recommended. In order to accommodate such recommendations, certified inspectors travel to the industrial site where the slings are used, then clean and visually inspect the same link by link for obvious wear and defects. Although an expert inspector can often detect visable wear and deformation of the sling components, such as a chain link that has been elongated by prolonged use, or a hook that has been weakened by tip loading, such inspections offer a minimum of protection and are not adequate for safety. Elements of the sling can become dangerously weakened by fatigue or minute cracks invisible to the unaided eye, and detectable only by more sophisticated procedures. Thus, in addition to frequent visual inspection, sling components in constant heavy use should be stress tested or examined under ultra-violet light by conventional magnetic flux procedure at intervals throughout the year to assure that they may be safely used up to their rated capacity.

Obviously where sling components sustain damage or fatigue that is not detectable by visual inspection, the potential exists for sling failure under a high tonage load and serious injury to nearby personnel.

In view of the reluctance in some instances of the owners and users of industrial slings to send their slings to an inspection and repair facility, the need for practical facilities to enable frequent comprehensive inspection of industrial slings above and beyond visual inspection at the industrial site where the sling is used has existed for many years, at least since the introduction of the overhead crane in heavy industry.

SUMMARY OF THE INVENTION

The present invention relates to the solution of the problem and long standing need mentioned above that, although apparently simple in retrospect, has escaped the art and the State and Federal regulatory authorities. In short, applicant has recognized the unwillingness of the art to bring its industrial slings to a testing laboratory for adequate inspection and repair and has solved the problem by developing facilities for testing slings at the industrial site where the slings are used.

To this end, applicant has provided a motor vehicle capable of carrying the heavy pull test equipment required for stress testing industrial slings having up to at least 50 tons of load capacity. The necessary test equipment, mounted on the vehicle, includes a heavy stress-resistant bed having fixtures at opposite ends for attachment to opposite ends of a sling component, such as a section of link chain, a hydraulic ram for exerting the testing force, a power driven pump for supplying the hydraulic pressure to the ram, a fuse box connectible with a source of electrical energy, suitable voltage transforming and current rectifying facilities for powering the inspection equipment, facilities for subjecting a sling or portion thereof to a magnetic field, and a source of ultraviolet light, by way of example, to enable testing for otherwise invisible cracks or flaws by conventional procedure known as magna-flux testing. The electrical power is usually supplied at 110 V or 220 V by the industrial facility that uses the sling, although the vehicle may also carry its own generator. To enable direct reading of the test force exerted on the sling component, a pressure gage associated with pressure supplied by the the hydraulic pump is preferably calibrated with respect to the dimensions of the ram to read in pounds of force exerted by the ram, as well as in pressure per square inch.

By virtue of applicant's assembly, industrial slings may be readily and economically tested at the industrial site where they are used. The on-site testing of many slings may be accomplished within a matter of hours rather than days. Not only is the time materially shortened that the sling is unavailable for use, but the expenses of additional handling and conveying of the sling between the industrial site and the test facility are eliminated at an appreciable saving to the industry. The reluctance of the industry to stress testing is overcome, such that slings may be adequately tested at frequent intervals throughout the year, depending upon the extent that the sling is used, thereby to assure a degree of safety that has not been achieved heretofore. Furthermore, the on-site testing enables the sling user to observe the test procedure and be assured that his sling has actually been properly tested.

Other details and advantages of this invention will be apparent from the following description and claims, reference being had to the accompanying drawings forming a part of this specification wherein like refer-

THE PRIOR ART

Pull test devices, per se, are well known, but no teaching is known of a pull test device for industrial slings that is mounted on a motor vehicle for transportation to the industrial site where the sling is used. Early examples of such testing machines for chains is illustrated in the Olsen U.S. Pat. No. 1,141,822, Jun. 1, 1915, and in Stutzer U.S. Pat. No. 2,824,446, Feb. 25, 1958. Cumulative examples of such test devices are found in Meldrum et al, U.S. Pat. No. 3,010,311, Nov. 28, 1961; and Rutledge et al, U.S. Pat. No. 4,475,404, Oct. 9, 1984. The latter patent illustrates a hydraulicly actuated pull test device for testing fiberglass rods.

Copies of the above noted patents are submitted herewith for consideration by the Examiner and to be made of record in this application.

BRIEF DESCRIPTION OF THE DRAWINGS

FIG. 1 is a perspective view illustrating a typical use of a sling lifting a multi-ton ingot.

FIG. 2 is a side elevation of a truck employed to house the sling test equipment and to convey the same to the industrial site for testing.

FIG. 4 shows a magna-flux booth for testing under ultraviolet light.

FIG. 5 is a fragmentary perspective view of a pull test bed mounted within the truck and protected by a heavy grating shown in a raised position.

Figure 3:
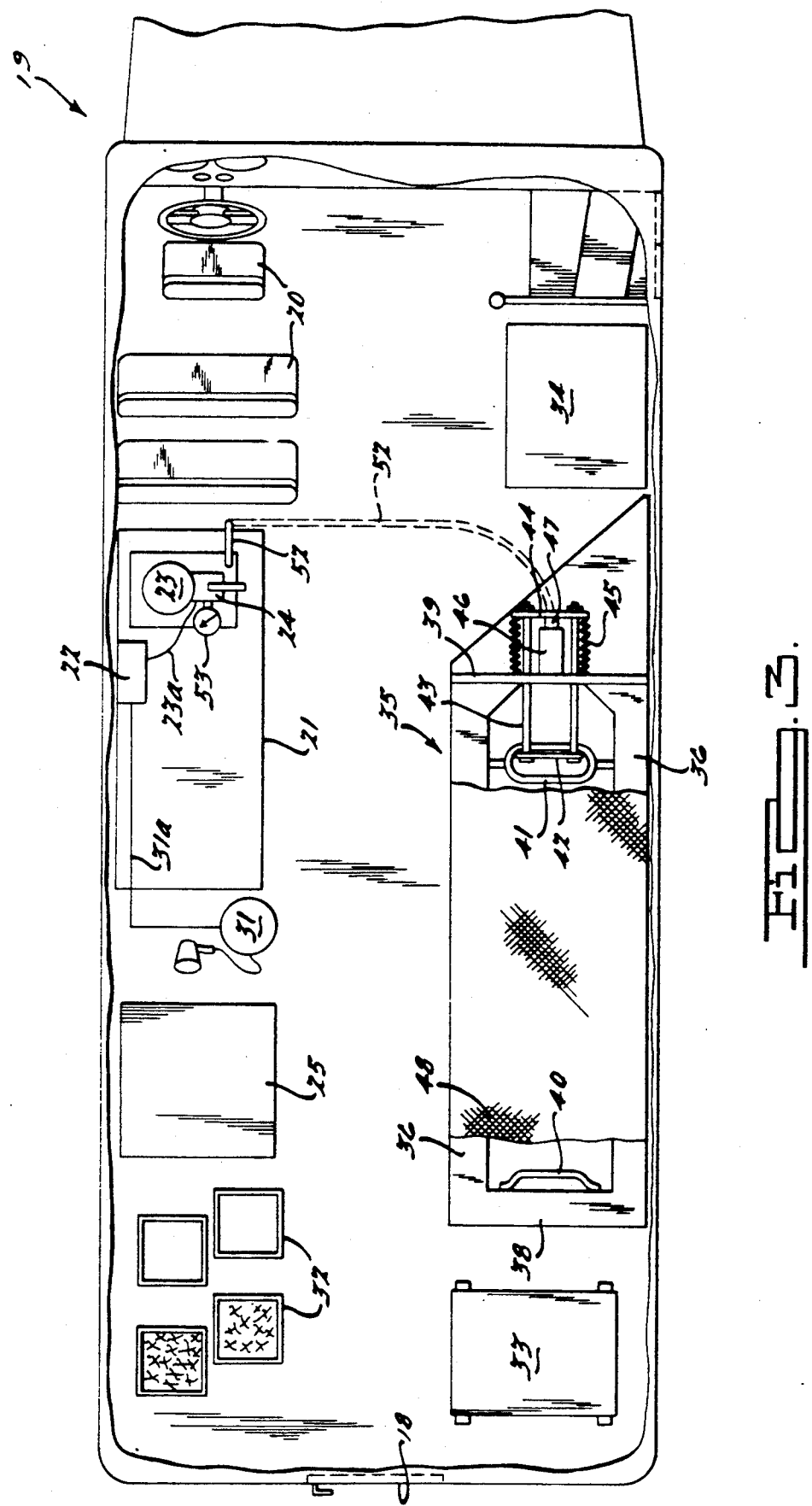
FIG. 3 is a schematic floor plan view of an arrangement of test facilities within the truck, with the top of the truck removed.

It is to be understood that the invention is not limited in its application to the details of construction and arrangement of parts illustrated in the accompanying drawings, since the invention is capable of other embodiments and of being practiced or carried out in various ways, and that the phraseology or terminology employed herein is for the purpose of describing the invention claimed in the appended claims.

DESCRIPTION OF A PREFERRED EMBODIMENT

Referring to the drawings, FIG. 1 illustrates a typical sling operation wherein a multi-ton steel ingot 10 is hoisted by a sling 11 secured to a heavy duty crane operated hook 12. Although the manufacturer of the sling 11 usually provides a 5:1 safety factor for the alloy steel links 13 in the chains 14, and an even greater safety factor for the enlarged master links 15 engaged by the crane hook 12 at the ends of the chains 14, it is apparent from FIG. 1 that the sling 11 can be improperly loaded so as to exceed its stress limit or to damage individual links 13.

For example, the angle A determines the linear force along the associated chains. Under any given load, the larger the angle A, the greater will be the linear stress on the chains 14. As the angle A approaches 180°, the stress on the chains 14 will approach infinity. Thus a link in a sling 11 rated to lift 40 tons, for example, could snap while attempting to lift a 25 ton ingot at a sufficiently large angle A. Furthermore, the link 13a in FIG. 1, by way of example, may be deformed by a sharp edge of the ingot 10 even if the overall stress on the sling 11 is within a safe limit.

Some slings employ a hook 17, FIG. 4, instead of a master link 15 for connection with the traveling crane or with other parts of the load to be lifted. If the hook 17 is not properly hooked at its bight, i.e., in the event of "tip loading" where the tip of hook 17 assumes the major load, the hook 17 itself may be deformed. Other factors may damage parts of the sling even when it is properly loaded, as for example a sudden upward jerk by the crane.

Inasmuch as damage to the sling may not always be readily apparent, frequent inspection of the sling components is important when the sling is in essentially continuous use. However, the reluctance of the owner or custodian of the sling to surrender it for the time required heretofore for testing has commonly resulted in the minimum annual testing required by OSHA (Occupational Safety and Health Act) with consequent occasional use of damaged slings and exposure of operating personnel to potential injury.

The above noted safety problem is avoided and a number of advantages, including reduced transportation cost and down time for the sling being tested, are achieved in accordance with the present invention by conducting the test at the industrial site where the sling is used. To this end, a motor vehicle 19 is provided, FIG. 2, which in the present instance is a large converted school bus with the passenger seats removed, except for a few for the driver and test personnel, FIG. 3. Although any motor truck capable of carrying the pull test equipment and having the floor space for conveniently carrying the auxiliary test equipment described herein may be used, a large passenger bus having a rear door 18 to facilitate loading and unloading of supplies and equipment, vertical head room to enable test personnel to work without crouching, and heavy duty spring suspension and tires for supporting the required load is particularly suitable.

FIG. 3 schematically illustrates a floor plan arrangement of the test equipment in the bus 19. Behind the remaining seats 20 for the driver, test personnel, and observers if any is a work bench and filing cabinet 21 for records and miscellaneous storage. Each chain 14 is identified by a metal tag secured thereto for recording important data, such as the recommended load limit and date and type of the last inspection. Confirming records are maintained by the test personnel. Minor repairs may be preformed on the work bench 21, but major repairs involving the replacement of a hardened alloy steel link 13 and the like will be preformed at a separate repair facility.

Above the bench 21 and adjacent to the bus sidewall is an energy reception means including a fuse box and transformer schematically indicated at 22 and adapted to be connected with a source of electrical power, usually supplied at 110 V or 220 V by the industrial facility that provides the sling 11 to be tested, although the necessary power may also be supplied by a generator carried by the bus 19. Also mounted on the bench 21 is a reservoir 23 for hydraulic fluid and an electric motor operated pump 24 for pressurizing the hydraulic fluid for use in a pull test.

Spaced rearwardly of bench 21 is a transportable booth 25 for examining chain components under ultraviolet light by conventional procedure. Details of the booth 25 are illustrated in FIG. 4 wherein a hook 26 suspended from the top of the booth is provided to support an element or sling components to be examined, such as the above mentioned hook 17. In accordance with conventional procedure, opposite ends of the element 17 to be examined are connected by suitable clamps 27 and 28, which in turn are connected to opposite poles of a current rectifier 29 for supplying the necessary magnetizing current.

Prior to magnetizing the element 17, it is cleaned, then coated with a liquid that is fluorescent under ultraviolet light and that contains a dispersion of magnetizable particulates, such that when magnetized, any interruption in the magnetic field caused for example by minute cracks in the element 17 that would not otherwise be visible, will be readily detected by observing the arrangement of the magnetized particulates under ultraviolet light. The ultraviolet light is produced by a hand held lamp 30 connected with a suitable source of electric power, including transformer 31 located adjacent to and transportable with the booth 25. The fluorescent glow of the magnetizable coating on the element 17 is best observed under dim light, so that a draw curtain may be provided to partially close the opening of the booth 25. The ultraviolet light apparatus and procedure for the ultraviolet inspection are well known to the art and the procedure is commonly referred to as magna-flux inspection. In some instances, it is not feasible to transport the article to be inspected under ultraviolet light to the truck 19. Consequently the booth 25 and associated equipment are portable to the article.

Adjacent to the rear door 18 of the bus 19 are storage bins 32 for chains 14 to be inspected or repaired, and a wheeled table 33 for transporting heavy chains 14 to and from the bus 19. Adjacent to the front of the bus 19 is a desk 34 where the inspector may record the type and results of the various tests and inspections.

Extending longitudinally of the bus 19 and for the major portion of its length between the desk 34 and table 33 is a heavy pull test bed 35 comprising a pair of laterally spaced stress resisting I-beams 36 suitably mounted on a platform 37 secured to the floor of the bus 19. Heavy steel cross plates 38 and 39 extend respectively across and are secured to the rearward and forward ends of the beams 36. A heavy fixed steel loop 40 is secured centrally to the plate 38 between the beams 36. A movable loop 41 is secured to a rectangular supporting plate 42 that in turn is bolted adjacent to its corners to four pull rods or stress rods 43, whereby the loops 40 and 41 are supported centrally within the pull test bed 35 at the same level above the platform 37.

The rods 43 extend in guided sliding relation from the plate 42 through the plate 39 and are bolted adjacent to the corners of a movable forward plate 44. The latter and rods 43 are normally urged rearwardly by return springs 45 secured under tension between the plates 39 and 44. Also mounted on the forward face of the plate 39 is a hydraulic cylinder 46 and ram 47 assembly capable of exerting a pulling force on the loop 41 of at least 50 tons.

The above described elements of the bed are capable of withstanding at least five times such a force and are dimensioned to enable pull testing of a chain 14 at least ten feet long. In order to prevent injury in the event that a chain being tested should snap and fly upwardly, a heavy steel protective grate 48 overlies the bed 35. The grate 48 is pivotally secured at 50 to an outer edge of the bed 35 adjacent to the bus wall and is counterbalanced by torsion springs 51 to facilitate its manual lifting, FIG. 5.

The rearward end of the cylinder 46 in advance of the ram 47 is hydraulically connected by a conduit 52 underlying the floor of the bus 19 and connected to the pump 24. Associated with the pressure of the pump 24 is a pressure gage 53 having a conversion scale calibrated with respect to the dimensions of the cylinder 46 and ram 47 to read in pounds of force exerted by the ram 47, as well as in pounds per square inch pump pressure.

In operation, electric power supplied by the industrial facility where the slings 11 are to be tested is plugged into the fuse box 22. If the power is supplied at 110 V, it is conducted directly by energy distribution means, including electric conductors 29a, 31a, and 23a to the rectifier 29, transformer 31, and to the motor of pump 24 respectively. If the power source is 220 V, it is first converted to 110 V by the transformer associated with the fuse box 22. A link chain or other sling component to be tested is then carefully cleaned and visually inspected link by link by a trained and certified inspector. If no visible defects are noted, the chain is extended between and suitably secured to the loops 40 and 41.

Hydraulic pressure from the pump 24 is then supplied with gradually increasing pressure to cylinder 46 to force the ram 47 gradually forwardly against plate 44, whereby the plates 42 and 44 connected by the stress rods 43 move the loop 41 forwardly and gradually stress the chain connected thereto. The chain under test will be rated for a specific load. The hydraulic pressure developed by pump 24 will be increased gradually until the chain being tested is subjected to twice its rated load, whereupon the chain can be certified as safely usable up to the certified load. Ordinarily, if a chain passes the pull test, assuring that it has a 2:1 safety factor over its rated safe load, every link of the chain is usually not subjected to the ultraviolet magna-flux testing. If a link appears to be slightly elongated, or if a hook or other sling component appears to be slightly deformed, possibly as a result of tip loading, that component is then examined under the ultraviolet light as described above.

I claim:

1. A self-contained mobile laboratory for on-site testing and certification of industrial slings comprising the combination of
   a) an operator driven motor vehicle having an enclosed housing, said housing having a floor, a roof, sidewalls, and a seat for said operator,
   b) a pull-test means within said housing comprising
      1) a stress resisting pull-test bed mounted on said floor adjacent to one of said sidewalls, said bed extending horizontally in a direction from front to rear linearly of said vehicle,
      2) a pair of attachment means spaced in said direction for attaching to linearly spaced portions of a sling component to be tested, said attachment means being movable relative to each other linearly of said bed, and
      3) force exerting means actuatable for moving said attachment means linearly of said bed and away from each other for pull testing said sling component when attached thereto,
   c) said floor having a floor space adjacent to and extending the length of said bed, said floor space and housing being dimensioned to enable movement of test personnel and observers therealong without crouching,
   d) storage means and desk means within said housing for storing test records and for enabling the recording of test data, respectively, e) magna flux means within said housing for rendering visible minute flaws in a component of said sling when said component is coated with a fluid sensitive to ultraviolet light and exposed to said light, said magna flux means comprising
   1) electrically powered means selectively operable for magnetizing said component, and
   2) electrically powered means selectively operable for illuminating said component with ultraviolet light, and
f) electrical circuit means within said housing for receiving electrical power and for selectively distributing power to said force exerting means for actuating the later and also for distributing power to said means for magnetizing and illuminating for operating the same.

2. The combination according to claim 1, said bed comprising a pair of load sustaining beams supported above said floor and extending side by side in said direction linearly of said housing, said beams providing a space therebetween for a sling component being tested in said bed between said beams, a protective cover for said bed having an outer edge adjacent to said one side wall and having an inner edge opposite said outer edge, said cover overlying said beams, and hinge means securing said outer edge adjacent to said one wall for swinging said inner edge upwardly from said bed to permit access thereto.

3. A self-contained mobile laboratory for on-site testing and certification of industrial slings comprising the combination of
   1) an operator driven motor vehicle having an enclosed housing defined by a floor having floor space for test and observer personnel to walk on, sidewalls and endwalls, a roof spaced above said floor space to enable said personnel to walk thereon without crouching, and a seat for a vehicle operator,
   2) essential equipment mounted in said housing in assembled operative condition to enable on site testing of industrial slings within said housing, said equipment including
      A) a pull-test bed mounted on said floor adjacent to said floor space and equipped with power operated apparatus for pull-testing sling components,
      B) electrically actuated power means for actuating said apparatus
      C) a work bench, a desk, and record storage space,
      D) magna-flux means for enabling visual detection of minute defects in a sling component, said magna-flux means including electrical means for magnetizing a sling component and electrical means for illuminating a sling component with ultraviolet light,
      E) electrical power reception and distribution means for receiving electrical power and for selectively distributing electrical power to said power means for actuating said apparatus, to said magnetizing means for magnetizing a sling component, and to said means for illuminating a sling component.

4. A mobile laboratory according to claim 3 wherein said pull-test bed extends horizontally within said housing, and comprising in addition a protective cover for said bed, said cover having an outer edge adjacent to one of said sidewalls and having an opposite inner edge, and hinge means securing said outer edge adjacent to said one wall for swinging said inner edge vertically to and from a protective position overlying said bed.

5. The method of on-site testing and certification of an industrial sling at the industrial site where the sling is used and of avoiding transportation of the sling to and from a remote test facility and the consequence cost and extended down time required for such transportation, the steps of
   1) providing an operator driven motor vehicle having an enclosed housing defined by a floor having a floor space for test and observer personnel to walk on, sidewalls, a roof spaced above said floor space to enable said personnel to walk on said floor space without crouching, and a seat for a vehicle operator,
   2) mounting within said housing equipment in assembled condition to provide a self-contained mobile laboratory for on-site testing and certification of sling components, said equipment including
      A) pull-test means including a pull-test bed mounted horizontally on said floor between said floor space and one of said sidewalls, and also including power actuated apparatus cooperable with said bed for pull-testing sling components,
      B) electrical power means for actuating said apparatus,
      C) a work bench and record storage space,
      D) magna-flux means for rendering visible minute flaws in a sling component, said magna-flux means including first electrical means for magnetizing a sling component, and a second electrical means for illuminating a sling component with ultraviolet light, and
      E) electric power reception and distribution means for receiving electrical power and for distributing electrical power to said electrical power means and to said first and second electrical means,
   3) transporting said vehicle to an industrial site where industrial slings are used,
   4) utilizing said equipment within said vehicle to test a sling at said site and in the presence of its custodian standing on said floor space,
   5) certifying the tested sling according to its safe usable load, and
   6) maintaining in said storage space a record for the tested sling.

* * * * *